United States Patent [19]
White et al.

[11] Patent Number: 4,677,054
[45] Date of Patent: Jun. 30, 1987

[54] METHOD FOR SIMPLE ANALYSIS OF RELATIVE NUCLEIC ACID LEVELS IN MULTIPLE SMALL SAMPLES BY CYTOPLASMIC DOT HYBRIDIZATION

[75] Inventors: Bruce A. White, Farmington, Conn.; F. Carter Bancroft, Brooklyn, N.Y.

[73] Assignee: Sloan-Kettering Institute for Cancer Research, New York, N.Y.

[21] Appl. No.: 521,103

[22] Filed: Aug. 8, 1983

[51] Int. Cl.$^4$ .................... C12Q 1/68; C12Q 1/02; C12N 15/00
[52] U.S. Cl. ........................ 435/6; 935/77; 935/78; 435/29
[58] Field of Search ............... 435/6, 29, 39; 436/63, 436/94; 935/76, 77, 78

[56] References Cited

U.S. PATENT DOCUMENTS

| | | | |
|---|---|---|---|
| 4,302,204 | 11/1981 | Wahl et al. | 435/172 X |
| 4,358,535 | 11/1982 | Falkow et al. | 435/5 |
| 4,483,920 | 11/1984 | Gillespie et al. | 435/6 |
| 4,533,628 | 8/1985 | Maas | 435/6 |

OTHER PUBLICATIONS

White, B. A. et al. *J. Biol. Chem.*, vol. 257, 15, 8569–8572, 1982.
Dobner, P. et al., *Proc. Natl. Acad. Sci.*, vol. 78, pp. 2230–2234, 1981.
Thomas, P. *Proc. Natl. Acad. Sci.*, vol. 77 pp. 5201–5205.
Southern, E. M., *J. Mol. Biol.*, vol. 98, pp. 503–517, 1975.
Noyes, B. E. et al., Cell, vol. 5, pp. 301–310, 1975.
Reiser, J. et al., *Bio. Chem. Biophys Res Comm.*, vol. 85, pp. 1104–1112, 1978.
Alwine, J. C. *Proc. Natl. Acad. Sci.*, vol. 74, pp. 5350–5354, 1977.
Brandsma, J. et al., *Proc. Natl. Acad. Sci.*, vol. 77, pp. 6851–6855, 1980.
Grunstein, M. et al., *Proc. Natl. Acad. Sci.* vol. 72, pp. 3961–3965, 1975.

*Primary Examiner*—Thomas G. Wiseman
*Assistant Examiner*—Jayme A. Huleatt
*Attorney, Agent, or Firm*—John P. White

[57] ABSTRACT

A simple technique for the simultaneous measurement of relative levels of a specific mRNA in numerous small samples of biological specimens is described. The technique involves denaturation of cytoplasmic preparations, followed by dotting of up to 96 samples onto a single sheet of nitrocellulose, hybridization with a $^{32}$P-labeled cDNA plasmid, autoradiography, and scanning. By analyzing cytoplasmic preparations instead of purified RNA, manipulations of multiple samples prior to analysis are minimized. Experiments with a clonal line of rat pituitary tumor (GH$_3$) cells show that this technique can be employed to follow the induction by Ca$^{2+}$ of prolactin mRNA sequences, employing cytoplasm prepared from as little as $2.5 \times 10^4$ cells. The specificity of the technique for prolactin mRNA is shown by employing GC cells, a GH$_3$ cell variant lacking detectable prolactin mRNA sequences. Experiments with cultured rat hemipituitaries show that the prolactin mRNA present in cytoplasm corresponding to as little as 1/100 of a pituitary can be readily detected. This technique is quite simple, can be quantified, and permits the simultaneous analysis of multiple samples while requiring very small amounts of material for analysis. Hence, it should be quite useful for example for studies with various experimental systems of the regulation of specific mRNA levels.

10 Claims, No Drawings

METHOD FOR SIMPLE ANALYSIS OF RELATIVE NUCLEIC ACID LEVELS IN MULTIPLE SMALL SAMPLES BY CYTOPLASMIC DOT HYBRIDIZATION

This work was supported by American Cancer Society Grant NP-271A, National Institutes of Health Grant GM 24442, Institutional Core Grant CA-08748 from the National Cancer Institute, Endocrine Research Training Grant AM 07313 SRC and Postdoctoral Fellowship AM 06770 from the National Institutes of Health. The U.S. Government has certain rights in this invention.

BACKGROUND

With the advent of recombinant DNA technology and the consequent availability of pure probes for the RNA products of specific genes, attention has been focused on the development of convenient and reliable methods for employing these probes to measure the concentrations of specific RNAs in animal cells or organs during induction by hormones, differentiation, etc. Techniques have been described for employing recombinant probes for solution hybridization measurements of absolute concentrations of the corresponding mRNA products of induced genes [Roop, D. R., et al (1978) Cell 15, 671-685; Beach L. R., and Palmiter, R. D. (1981) Proc. Nat'l. Acad. Sci. U.S.A. 78, 2110-2114]. However, for many investigations, measurements of relative mRNA concentrations (experimental/control) can yield the requisite information. Present techniques for this measurement involve either end-labeling of purified RNA with $^{32}P$, followed by hybridization to an unlabeled immobilized recombinant plasmid (Williams, J. G. et al. (1979) Cell 17, 903-913), or hybridization of a $^{32}P$-labeled recombinant plasmid to unlabeled purified RNA which has been either dotted directly to nitrocellulose or transferred to nitrocellulose following gel electrophoresis (Thomas, P. S. (1980) Proc. Nat'l. Acad. Sci. U.S.A. 77, 5201-5205; Dobner, P. R., et al. (1981) Proc. Nat'l. Acad. Sci. U.S.A. 78, 2230-2234).

Analysis of specific mRNA levels by any of these techniques requires that RNA first be isolated, usually by phenol extraction, from a large sample of the cells or tissue under investigation. However, many studies of regulation of specific gene expression, as for example replicate determinations of the time course or dose-response curves of a hormonal induction, require analysis of specific mRNA levels in numerous samples. Purification of RNA from samples of cells and tissues can be a difficult and time-consuming process, involving multiple phenol extractions, precipitation, recovery, and gel electrophoresis prior to analysis. (See for example, Penman, S. J. Mol. Biol. 17, 117 (1966). Brandsma et al., PNAS, U.S.A., 77, 6851 (1980) try whole animal cells dotted to nitrocellulose to detect EBV (Epstein—Barr Virus) but this method yields variable signals in replicate samples i.e. reproducibility is poor. Therefore, the Brandsma method is unsuited for quantitative analysis. Thus, it would be desirable to have available a technique for the simultaneous analysis of relative levels of an mRNA species in multiple samples, which requires both minimum amounts of sample such as of cells or tissue and minimal manipulation of each sample prior to analysis. For many types of regulation experiments, multiple sample analyses are involved.

SUMMARY

We describe here the technique, termed cytoplasmic dot hybridization, of the present invention, whereby a $^{32}P$-labeled cDNA plasmid can be used to measure relative concentrations of the corresponding mRNA in unfractionated cytoplasm prepared either from cultured animal cells or from animal tissue. Cellular cytoplasm is readily prepared from many kinds of cells by brief treatment in isotonic or hypotonic buffer containing 0.5% Nonidet P-40 (NP-40) nonionic detergent (Sigma Chemical Co., P. O. 14508 St. Louis, Mo. or Shell Chemical Company, W. Orange, N.J.). The chemical name for NP-40 is octylphenoxypolyethoxyethanol. Since it is not necessary to recover RNA the method can be applied to very small samples of cells and tissues. The technique is quite convenient, and can be used for the analysis of up to 96 samples simultaneously. It involves denaturation of the cytoplasm, dotting onto nitrocellulose and hybridization to a $^{32}P$-labeled complementary DNA hybrid plasmid. The method can be applied to measure relative mRNA levels in cytoplasm isolated from as little as $2.5 \times 10^4$ cultured cells such as, for example prolactin mRNA levels in: (1) cultured rat pituitary tumor ($GH_3$) cells or (2) from 100 microgram of tissue or (3) as little as 1/100 of a rat pituitary, i.e. the method is useful for mixed cell populations.

DESCRIPTION

The technique of the present invention is described as applied to $GH_3$ cultured rat pituitary cells; this is for illustrative purposes only and is not meant to limit the invention. It will be obvious to those skilled in the art that the method of the present invention is general in scope and can be used for DNA and mRNA-like analysis of all sorts of biological specimens i.e. plant and animal cells and tissues. For instance, Burch et al [Cell, 33:65 (1983)] apply the method to liver RNA of chicken embryos citing the work of White and Bancroft (1982) Supra. Rowe uses the method to detect collagen RNA in rat osteosarcoma cells (unpublished observations). Heywood measures small cytoplasm RNA and quantifies (in press). Xu, et al. (Biochem. Biophys. Res. Comm. 111 624–629 (1983) use it in rat prostrate to measure mRNA for testosterone dependent proteins. Also at the Harvard Medical School, Cochran et al. [Cell, 33, 939–947 (1983)] use the method of the present invention in mouse fibroblast systems to study genes regulated by platelet-derived growth factor. Thus above references demonstrate the wide applicability and utility of the present invention. Also obvious is the wider use of the method as a probe for RNA in biological specimens or for the RNA product of recombinant DNA synthesis methods. The method is also of use for biological materials such as single or mixed cell cytoplasms, single or mixed cell populations, and single or mixed cell-free systems. Therefore, this method is useful as a probe for RNA or DNA in systems containing other molecular components since RNA need not be purified to be determined, assayed or quantified by the present invention. Very small amounts of sample can be tested. Furthermore, the samples can be hybridized with multiple probes used in sequence.

This method is described in a publication, White and Bancroft J. Biol. Chem., 257, 8569 (1982) which is herein incorporated by reference.

$GH_3$ cells $(1-10\times10^6)$ are pelleted by centrifugation (600 $\times$g, 5 min), resuspended in 1.0 ml of phosphate-buffered salts (Dobner, Supra), and repelleted by centrifugation in a sterile, 1.5-ml tube (15,000 $\times$g, 15 sec in an Eppendorf Model 3200 Zentrifuge). The above applies to suspension culture cells or monolayer cells suspended by scraping with a rubber policeman. After resuspension in 45 microliters of ice-cold 10 mM Tris (pH 7.0), 1 mM EDTA, cells are lysed by addition of two 5-microliter aliquots of 5% NP-40 with 5 min of mixing on ice in between. However, one minute may be sufficient. The second 5 microliter aliquot of NP-40 may not be necessary. It is very important that the cells be thoroughly suspended before addition of NP-40 to avoid formation of intractable cell clumps. Following pelleting of nuclei (15,000 $\times$g, 2.5 min), 50 microliter of the supernatant are transferred to a sterile 1.5-ml tube containing 30 microliters of 20$\times$NaCl/Cit [1 $\times$NaCl/Cit is 0.15M NaCl/0.015M trisodium citrate i.e. standard saline citrate (SSC)]plus 20 microliters of 37% (w/w) formaldehyde (Fisher No. F-79). The 20$\times$SSC-formaldehyde solution is freshly prepared just before use. The mixture is then incubated at 60° C. for 15 min, and stored at $-70°$ C. For analysis, 5-20 microliters of each sample are serially diluted with 15$\times$NaCl/Cit in a 96-well microtiter plate to yield a final volume of 150 microliter. 100 microliter of each dilution are applied with suction to a 4-mm diameter spot on a nitrocellulose sheet (BA45,0.45 micrometer pore diameter) supported on a No. 470 paper employing a 96-hole Minifold apparatus, all from Schleicher and Schuell (S&S) Kline, N.H. 03431). The nitrocellulose sheet is then baked (80° C., 90 min) in vacuo to fix cytoplasmic macromolecules (Thomas, Supra). The sample as so affixed is durable and can be stored in a desiccator. Prehybridization of the nitrocellulose, preparation by nick translation of the $^{32}$P-labeled pPRL-1 DNA (PRL=Prolactin) probe (specific activity, 1-2$\times10^8$ cpm/microgram), hybridization, autoradiography, and quantitation by scanning are performed as described previously (Dobner, Supra). It is possible to re-use the nitrocellulose with the RNA (or other nucleic acid) attached thereon for different probes by boiling the nitrocellulose for about 10 min. in hybridization buffer thereby removing the previous radioactive nucleic acid hybridization probe with little loss of bound nucleic acid sample. Another probe can then be used with the same samples. NP-40 is a non-ionic detergent. It will be obvious to substitute another such as Triton-x. Other denaturing agents such as glyoxal can be substituted for formaldehyde. Other nucleic acid binding substrates obviously can substitute for nitrocellulose such as diazobenzyloxymethyl substrates.

As in work in purified RNA, it is a good idea to sterilize all solutions and glassware, either by autoclaving or treatment with diethylpyrocarbonate to destroy any RNase present. Cytoplasm from the above $GH_3$ cells does not appear to have any RNase activity (White and Bancroft Supra). When working with biological specimens containing high endogenous RNase activity, an RNase inhibitor should be present. Addition of the potent ribonuclease inhibitor vanadylribonucleoside complex [Berger, S. L. and C. S. Birkenmeir (1979) Biochem. 18, 5143]to a final concentration of 0.1 mM does not interfere with the signal obtained by the method as described above.

The technique is also described in the following example as applied to rat pituitary cytoplasmic extracts containing source biological material from mixed cell populations. It will be obvious to those skilled in the art that in general, all manner of biological specimens and/or systems containing biological type molecular components which contain denaturable RNA, mRNA, and/or mRNA-like molecules, lend themselves to analysis by this invention. In the same manner, the method lends itself to analysis of RNA in enucleated cells.

Sprague-Dawley rats are stunned and killed by decapitation. The pituitary is removed into sterile serum-free medium (White, et al., (1981) J. Biol. Chem. 256, 5942), and the anterior lobe (pars distalis) is teased away from the posterior lobe and split into hemipituitaries. After 4 days of culture on stainless steel rafts (Nicoll, C. S., and Meites, J. (1962) Endocrinology 70, 272–277) in serum-free medium (White, (1981) Supra), each hemipituitary is transferred to a sterile 1.5-ml tube and stored at $-70°$ C. For analysis, each hemipituitary is homogenized in a 100–1000–microliter capacity homogenizer (Radnoti Glass, Monrovia, CA) containing 50 microliters of 10 mM Tris (pH 7.0), 1 mM EDTA, 0.5% NP-40, with 10 revolutions of the pestle. The contents are transferred to a sterile 1.5-ml tube and incubated for at least 1 min on ice. Following pelleting of the nuclei by centrifugation (15,000 $\times$g, 2.5 min), the cytoplasm is analyzed as described above for $GH_3$ cells.

Applying denatured cytoplasm obtained by the above technique to BA85 nitrocellulose (Schleicher and Schuell) using the Minifold apparatus is illustrated in the following manner:

1. A piece of S&S BA85 (0.45 micrometer pore size), avaiable precut to the size of the S&S Minifold apparatus (4 in.$\times$5¼in.), is prewetted in $H_2O$, then in 15 $\times$SSC.

2. Dilutions of cytoplasm are made in wells of a microtiter plate (Falcon #3911 Microtest III), each containing 15$\times$SSC. The first dilution is 10 micrbliters cytoplasm into 190 microliter 15$\times$SSC. As first shown by Thomas, Supra, RNA will bind to nitrocellulose in the presence of this high salt concentration.

3. One piece of S&S #470 paper, pre-wet with 15$\times$SSC, is placed on the Minifold, and the BA85 nitrocellulose sheet is placed on top. The top part of the Minifold is then clamped in place, and house line vacuum is applied.

4. An 80 microliter aliquot of each sample is applied. (100 out of a 150 microliters if such be the dilutions as shown above). In general, a sample containing cytoplasm from in excess of approximately $5-8\times10^5$ $GH_3$ cells tends to block flow through the filter. To avoid getting haloes instead of uniform circles, and getting air bubbles trapped in the holes, pipet the sample at a steady rate directly into the center of the hole.

5. After turning off the suction, the Minifold is unclamped, and the nitrocellulose is placed between two sheets of S&S #470 paper. Following stapling around the edges of the paper, this is baked in a vacuum oven at 80° for 90 minutes to retain RNA on the nitrocellulose during subsequent steps.

The hybridization protocol is essentially the same as is employed in RNA dot analysis (Thomas, Supra and Dobner, Supra). Prehybridization of the nitrocellulose, followed by hybridization for two days with a $^{32}$P-labeled complementary DNA hybrid plasmid, are performed as described by Wahl et al. (1979) Proc. Nat'l. Acad. Sci. U.S.A. 76, 3683 except that we normally do not include dextran sulfate, and glycine is omitted. The nitrocellulose is then exposed at −70° C. to Kodak XAR-2 film, using an intensifying screen. The resultant dots are scanned with a modified Helena TLC Quick Scan densitometer.

To determine both the feasibility of and optimal conditions for the technique, aliquots of GH$_3$ cell cytoplasm were either untreated or denatured by heating at 60° C. with either formaldehyde (7.4%) or glyoxal (8%) for various times and then applied to nitrocellulose, hybridized with $^{32}$P-labeled rat prolactin cDNA plasmid pPRL-1 (Maurer, R. A., et al. (1980) J. Biol. Chem. 225, 2243–2246), and autoradiographed. Nondenatured cytoplasm yielded a barely detectable spot, while denaturation by incubation with formaldehyde for at least 5 min yielded a dramatic increase in the spot intensity. Substitution of glyoxal for formaldehyde yielded a smaller increase in the spot intensity at all denaturation times tested (See FIG. 1 White (1982) Supra). The spot intensities of glyoxal-denatured samples were not increased by prehybridization at pH 8.0 instead of pH 6.5 (data not shown), in agreement with the observations of Thomas, Supra. Since the maximum spot intensity was obtained after 10 or 15 min of formaldehyde denaturation (FIG. 1, White, (1982) Supra), a standard procedure involving a 15-min denaturation at 60° C. with 7.4% formaldehyde was employed for subsequent experiments. It can also be seen in FIG. 1 (rows 1–3) ibid that samples containing successive 2-fold dilutions of cytoplasm yielded coresponding successive decreases in the spot intensities, implying that the technique can be employed for quantitative analysis.

The results of two control experiments show that the technique specifically detects prolactin mRNA sequences in the macromolecular mixture present in unfractionated cytoplasm prepared from GH$_3$ cells. Reduction of the spot intensity to undetectable levels in cytoplasmic preparations preincubated with RNase (FIG. 1, row 4, White (1982) Supra) shows that the signal is due to hybridization of the probe to RNA. The specificity of the technique for prolactin mRNA was shown by applying it to GC cells. The GC cell line is a clonal variant of the GH$_3$ cells (Bancroft, F. C. (1981) in Functionally Differentiated Cell Lines (Sato, G., ed) pp. 47–59, Alan R. Liss, Inc., New York) which has been shown by both solution hybridization (Evans, G. A., and Rosenfeld, M. G. (1979) J. Biol. Chem. 254, 8023–8030) and gel analysis by the "Northern technique" [Alwine et al., (1977) Proc. Nat'l. Acad. Sci. U.S.A. 74, 5350](unpublished observations B. A. White) to contain undetectable levels of prolactin mRNA. The observation of a barely detectable spot (FIG. 1, row 5, White (1982) Supra) when cytoplasm prepared from GC cells was analyzed on the same nitrocellulose sheet as GH$_3$ cell cytoplasm shows that the signal obtained with GH$_3$ cell cytoplasm was due almost entirely to hybridization of the probe to prolactin mRNA sequences. There is thus an extremely low level of non-specific background hybridization yielding barely detectable spots in controls. In prolactin systems for example, this control is less than 0.3%.

An experiment was performed to determine whether the use of cytoplasmic preparation instead of purified RNA in the present procedure results in a decrease in the sensitivity of detection of prolactin mRNA sequences. Cytoplasm was prepared from one aliquot of a GH$_3$ cell culture as described above. Total cytoplasmic RNA was prepared by phenol extraction (Dobner, Supra) from another aliquot of cells from the same culture. Both samples were then denatured with formaldehyde and subjected to dot hybridization on the same nitrocellulose sheet, and the intensities of the resulting spots were quantitated by scanning, all as described above. Cytoplasm from 1, 2, and $4 \times 10^5$ cells and total cytoplasmic RNA extracted from the same numbers of cells were analyzed in duplicate. The average intensity of the cytoplasmic spots was 0.8 times the average intensity of the corresponding RNA spots. Hence, cytoplasmic dot hybridization appears to be as sensitive as RNA dot hybridization. There appears to be no masking effect by non-specific cellular RNA on mRNA sequences i.e. no interference with the hybridization reaction.

The technique can be used to quantify specific mRNA induction. The following example applies the quantitative aspect of the technique to GH$_3$ cells and is for illustrative purposes only and is not meant to limit the invention. The method can be quantified for RNA from all manner of biological specimens such as single or mixed cell cytoplasms, single or mixed cell populations, and single or mixed cell-free systems. The application of the method to quantify RNA in source material from mixed systems is very useful (White (1982) Supra and Burch (1983) Supra). Essentially it can screen multiple samples for a particular RNA.

We have previously shown with an RNA gel blot hybridization technique that incubation of GH$_3$ cells with calcium causes a sizable increase in cytoplasmic prolactin mRNA sequences (White, (1981) Supra). The present technique was employed to analyze the calcium-induced stimulation of prolactin mRNA sequences in GH$_3$ cells. The observations (FIG. 2 White (1981) Supra and Table I below) that, at a sufficiently low input of cytoplasm, the spot intensities were proportional to the amount of cytoplasm applied, for both experimental and control samples, support the validity of the present technique.

TABLE I

QUANTITATION BY CYTOPLASMIC DOT HYBRIDIZATION OF PROLACTIN mRNA INDUCTION IN GH₃ CELLS

| Number of cells | $-CaCl_2$ (control) | $+CaCl_2$ |
|---|---|---|
| $5 \times 10^4$ | 1.0 | 8.3 |
|  | 1.5 | 10.1 |
| $1 \times 10^5$ | 3.2 | 21.9 |
|  | 4.3 | 25. |
| $2 \times 10^5$ | 5.2 | 37. |
|  | 8.2 | 45.4 |
| $4 \times 10^5$ | 9.1 | 52. |
|  | 14. | 69.8 |

Legend to Table I: GH₃ cells were incubated in serum-free, calcium-free medium for 3 days and then in the same medium for 5 days in the presence ($+CaCl_2$) or absence ($-CaCl_2$) of 0.4 mM $CaCl_2$, as shown by White (1981) Supra. Cytoplasmic aliquots prepared from cells in either culture were analyzed in duplicate for prolactin mRNA as described above. The same microdensitomer readings from autoradiographic spots (3 day exposure) are used for Table I and FIG. 2, White (1982) Supra. Autoradiographic spots obtained with equal quantities of cytoplasm prepared from GC cells and analyzed on the same nitrocellulose sheet were undetectable.

Its validity was further investigated by comparing the induction of prolactin mRNA sequences calculated from the initial slopes of the curves shown in FIG. 2, ibid with the induction measured when total cytoplasmic RNA isolated from cells from the same cultures was analyzed by the RNA gel blot hybridization procedure we have described previously (Dobner, Supra; White, (1981) Supra). The induction values observed were 14-fold and 17-fold, respectively. This good agreement means that both techniques measure prolactin mRNA. Furthermore, if known amounts of the specific plasmid DNA in sequential dilution are spotted onto the same nitrocellulose paper as used to detect RNA, the number of specific mRNA molecules per cell can be determined since the sequential dilution DNA spots can be used as a reference guide. For example, the prolactin system as described above can be quantified in this manner.

For many biochemical investigations, it would be useful to be able to employ a single tissue or organ to measure the value of a given parameter, so that an experimental and a control value could be obtained with the tissue or organ of a single animal. For example, a single pituitary divided into hemipituitaries will provide both experimental and control materials. Previous investigations of the regulation of specific mRNA levels in the pituitary gland have employed extraction of RNA from the pituitaries of a number of animals for each experimental point. The cytoplasmic dot hybridization technique can be employed to detect the prolactin mRNA in cytoplasm prepared from a single rat hemipituitary. By analyzing successive dilutions of such preparations, it was observed that, in fact, the prolactin mRNA present in a little as 1/100 of either a male or female rat pituitary which had been cultured for 4 days could be easily detected by this technique (FIG. 3 White (1982) Supra). As with GH₃ cell cytoplasm, treatment of pituitary cytoplasm with RNase reduced the hybridization signal to undetectable levels (data not shown). As might be expected, female pituitaries tended to yield more intense spots than male pituitaries. Therefore, it will be obvious to those skilled in the art that the method is applicable to glands and tissues obtained from a single animal or plant.

Applications of the method include screening for changes in specific mRNA levels during (1) hormonal induction, (2) organ development, and (3) differentiation and traversal of the cell cycle; as well as screening multiple samples of tissues, tissue biopsies, blood samples etc. for the expression of oncogenes or viral genes for their RNA products. It will also be obvious to use the method to measure DNA sequences in biological materials where the DNA need not be purified prior to application of this method. For instance, one could measure pro-viral DNA sequences in biological preparations or specimens. Convenience of the method is high since (1) cytoplasm can be prepared and frozen and then analyzed, (2) samples baked onto nitrocellulose can be stored, (3) samples baked onto nitrocellulose can be re-used to provide sequential analysis with multiple labelled nucleic acid probes of a plurality of target nucleic acids in samples of biological materials.

What is claimed:

1. A process for qualitative or quantitative detection of a target ribonucleic acid in an eucaryotic cytoplasmic sample, which has been substantially freed of whole cells and cell nuclei consisting essentially of:
   (a) obtaining a sample containing whole eucaryotic cells;
   (b) separating whole cells and cell nuclei from the cytoplasmic sample to form a cell-free, nuclei-free cytoplasmic sample;
   (c) denaturing said cytoplasmic sample:
   (d) applying the denatured cytoplasmic sample directly onto a nucleic acid binding substrate;
   (e) incubating the bound cytoplasmic sample with a labelled probe, complementary to a target ribonucleic acid, under hybridizing conditions; and
   (f) measuring the degree of hybridization.

2. A process for analyzing a plurality of denatured eucaryotic cytoplasmic samples, each containing a target ribonucleic acid, in which the samples have been substantially freed of whole cells and cell nuclei consisting essentially of:
   (a) obtaining a plurality of samples containing whole eucaryotic cells;
   (b) separating whole cells and cell nuclei from the cytoplasmic samples to form cell-free nuclei-free cytoplasmic sample;
   (c) separately denaturing each cytoplasmic sample;
   (d) applying each denatured cytoplasmic sample directly onto a common nucleic acid binding substrate;
   (e) sequentially incubating the bound cytoplasmic samples with a series of labelled probes, each complementary to a target ribonucleic acid, under hybridizing conditions; and
   (f) measuring the degree of hybridization.

3. Process of claims 1 or 2 wherein the eucaryotic cytoplasmic sample free of whole cells and cell nuclei is prepared by suspending each sample containing whole eucaryotic cells thoroughly in cold buffer, lysing the cells and removing any cell nuclei.

4. Process of claim 3, wherein an RNase inhibitor is present subsequent to cell lysis.

5. Process of claim 4 wherein the cells are lysed with non-ionic detergent.

6. Process of claims 1 or 2 wherein the eucaryotic cytoplasmic sample is denatured with saline-citrate buffer, containing denaturing agents selected from the group consisting of formaldehyde and glyoxal, freshly prepared on the day of each assay.

7. Process of claims 1 or 2 wherein each denatured eucaryotic cytoplasmic sample is applied to a nucleic acid binding substrate prewet with a saline-citrate buffer.

8. Process of claim 7 wherein heat is subsequently applied to the nucleic acid binding substrate.

9. Process of claims 1 or 2 wherein the nucleic acid binding substrate is selected from the group consisting of nitrocellulose and diazobenzyloxymethyl substrates.

10. Process of claims 1 or 2 wherein the eucaryotic cytoplasmic sample is selected from the group consisting of cell-free systems, tissue specimens, organs from a single animal or plant, mixed-cell systems and cytoplasmic preparations.

* * * * *